(12) United States Patent
Hanajima

(10) Patent No.: US 11,335,459 B2
(45) Date of Patent: May 17, 2022

(54) SURGICAL INSTRUMENT SET AND INSTRUMENT MANAGEMENT SYSTEM

(71) Applicant: DGSHAPE Corporation, Hamamatsu (JP)

(72) Inventor: Masaki Hanajima, Hamamatsu (JP)

(73) Assignee: DGSHAPE CORPORATION, Shizuoka (JP)

( * ) Notice: Subject to any disclaimer, the term of this patent is extended or adjusted under 35 U.S.C. 154(b) by 539 days.

(21) Appl. No.: 16/524,222

(22) Filed: Jul. 29, 2019

(65) Prior Publication Data

US 2020/0043603 A1 Feb. 6, 2020

(30) Foreign Application Priority Data

Aug. 1, 2018 (JP) .............................. JP2018-144919

(51) Int. Cl.
*G06F 9/44* (2018.01)
*G06Q 10/00* (2012.01)
*G06F 9/00* (2006.01)
*G06F 15/177* (2006.01)
*G16H 40/40* (2018.01)
*A61B 90/98* (2016.01)
*A61B 90/90* (2016.01)

(52) U.S. Cl.
CPC ............. *G16H 40/40* (2018.01); *A61B 90/90* (2016.02); *A61B 90/98* (2016.02)

(58) Field of Classification Search
CPC ........ G16H 20/40; A61B 34/10; A61B 90/98; A61B 34/25; A61B 2090/365
See application file for complete search history.

(56) References Cited

U.S. PATENT DOCUMENTS 10,837,974 B2 * 11/2020 Postma .............. G06Q 30/0641

FOREIGN PATENT DOCUMENTS

| JP | 2003-16198 A | 1/2003 |
| JP | 2009-72338 A | 4/2009 |
| JP | 2012-215990 A | 11/2012 |
| JP | 2013-116234 A | 6/2013 |
| JP | 3199614 U | 9/2015 |
| JP | 2015-197735 A | 11/2015 |

OTHER PUBLICATIONS

Wang et al., Towards Occlusion-Free Surgical Instrument Tracking: A Modular Monocular Approach and an Agile Calibration Method, 8 pages (Year: 2015).*

* cited by examiner

*Primary Examiner* — Thuy Dao
(74) *Attorney, Agent, or Firm* — Keating & Bennett, LLP

(57) ABSTRACT

A system includes a first memory to store instrument IDs associated in a one-to-one correspondence with instruments, a second memory to store set IDs associated in a one-to-one correspondence with surgical instrument sets each including a plurality of instruments, a third memory to store work histories of the instruments each identified by a respective one of the instrument IDs, each of the work histories stored in association with the respective one of the instrument IDs and including work information about repair work, and a fourth memory to store work histories of the surgical instrument sets each identified by a respective one of the set IDs, each of the work histories stored in association with the respective one of the set IDs and including work information about repair work.

18 Claims, 7 Drawing Sheets

420

| SET ID | INSTRUMENT ID | PARTS ID | COLLECTION LOCATION | USER ID | WORK DATE AND TIME |
|---|---|---|---|---|---|
| Set1 | - | - | area211 | A123456 | 2017/5/11 19:55:00 |
| Set1 | BOM1 | - | area211 | A123456 | 2017/5/11 19:51:00 |
| Set1 | BOM2 | - | area211 | A123456 | 2017/5/11 19:53:02 |
| Set1 | BOM3 | - | area211 | A123456 | 2017/5/11 19:51:50 |
| Set1 | BOM4 | - | ... | ... | ... |
| Set1 | BOM4 | SX1 | ... | ... | ... |
| Set1 | BOM4 | SX2 | ... | ... | ... |
| Set1 | BOM4 | SX3 | ... | ... | ... |
| Set1 | BOM4 | SX4 | ... | ... | ... |
| Set2 | - | - | ... | ... | ... |
| Set2 | COM1 | - | ... | ... | ... |
| Set2 | COM2 | - | ... | ... | ... |
| ... | ... | ... | ... | ... | ... |
| ... | ... | ... | ... | ... | ... |
| ... | ... | ... | ... | ... | ... |
| ... | ... | ... | ... | ... | ... |
| ... | ... | ... | ... | ... | ... |

FIG. 3

| 401 | 402 | 403 | 404 | 405 | 406 | 407 | 408 | 409 |
|---|---|---|---|---|---|---|---|---|
| | | | | | | | | |
| SET ID | SURGICAL INSTRUMENT SET NAME | INSTRUMENT ID | INSTRUMENT NAME | PARTS ID | GS1 CODE | IMAGE FILE | ATTRIBUTE 1 | ATTRIBUTE 2 |
| Set1 | Set A | -- | -- | -- | -- | Set1.jpg | Hospital A1 | Department C1 |
| Set1 | Set A | BOM1 | Set1BOM1 | -- | 12345678901234567890123456 | Set1BOM1.jpg | Hospital A1 | Department C1 |
| Set1 | Set A | BOM2 | Set1BOM2 | -- | 13579098765432345678098765 | Set1BOM2.jpg | Hospital A1 | Department C1 |
| Set1 | Set A | BOM3 | Set1BOM3 | -- | 12345678765434567876234560 | Set1BOM3.jpg | Hospital A1 | Department C1 |
| Set1 | Set A | BOM4 | Set1BOM4 | -- | 98765434543222345678900998 | Set1BOM4.jpg | Hospital A1 | Department C1 |
| Set1 | Set A | BOM4 | Set1BOM4 | SX1 | 12345678909876543456765665 | Set1BOM4SX1.jpg | Hospital A1 | Department C1 |
| Set1 | Set A | BOM4 | Set1BOM4 | SX2 | ... | Set1BOM4SX2.jpg | Hospital A1 | Department C1 |
| Set1 | Set A | BOM4 | Set1BOM4 | SX3 | 12345678909876543456765667 | Set1BOM4SX3.jpg | Hospital A1 | Department C1 |
| Set1 | Set A | BOM4 | Set1BOM4 | SX4 | ... | Set1BOM4SX4.jpg | Hospital A1 | Department C1 |
| Set2 | Retractor | -- | -- | -- | -- | Set2.jpg | Hospital A2 | Department C1 |
| Set2 | Retractor | COM1 | Retractor Part 1 | -- | 10293847561029384756555555 | Set2COM1.jpg | Hospital A2 | Department C1 |
| Set2 | Retractor | COM2 | Retractor Part 2 | -- | 10293847561029384756555556 | Set2COM2.jpg | Hospital A2 | Department C1 |
| ... | ... | ... | ... | ... | ... | ... | ... | ... |
| ... | ... | ... | ... | ... | ... | ... | ... | ... |
| ... | ... | ... | ... | ... | ... | ... | ... | ... |

| SET ID | INSTRUMENT ID | PARTS ID | COLLECTION LOCATION | USER ID | WORK DATE AND TIME |
|---|---|---|---|---|---|
| Set1 | – | – | area211 | A123456 | 2017/5/11 19:55:00 |
| Set1 | BOM1 | – | area211 | A123456 | 2017/5/11 19:51:00 |
| Set1 | BOM2 | – | area211 | A123456 | 2017/5/11 19:53:02 |
| Set1 | BOM3 | – | area211 | A123456 | 2017/5/11 19:51:50 |
| Set1 | BOM4 | – | ... | ... | ... |
| Set1 | BOM4 | SX1 | ... | ... | ... |
| Set1 | BOM4 | SX2 | ... | ... | ... |
| Set1 | BOM4 | SX3 | ... | ... | ... |
| Set1 | BOM4 | SX4 | ... | ... | ... |
| Set2 | – | – | ... | ... | ... |
| Set2 | COM1 | – | ... | ... | ... |
| Set2 | COM2 | – | ... | ... | ... |
| ... | ... | ... | ... | ... | ... |
| ... | ... | ... | ... | ... | ... |
| ... | ... | ... | ... | ... | ... |
| ... | ... | ... | ... | ... | ... |
| ... | ... | ... | ... | ... | ... |

FIG.5

| SET ID | INSTRUMENT ID | PARTS ID | PACKAGING MATERIAL | STERILIZATION METHOD | STERILIZATION CONDITION | EFFECTIVE PERIOD | USER ID | WORK DATE AND TIME |
|---|---|---|---|---|---|---|---|---|
| Set1 | -- | -- | case1 | G1 | GD1 | 6 months | A123456 | 2017/5/11 19:50:00 |
| Set2 | -- | -- | case1 | G1 | GD1 | 6 months | A123456 | 2017/5/11 19:51:00 |
| Set3 | -- | -- | case1 | G1 | GD1 | 6 months | A123456 | 2017/5/11 19:53:02 |
| Set4 | -- | -- | case1 | G1 | GD1 | 6 months | A123456 | 2017/5/11 19:51:50 |
| Set5 | -- | -- | case1 | G1 | GD1 | 6 months | ... | ... |
| Set6 | -- | -- | case1 | G1 | GD1 | 6 months | ... | ... |
| Set7 | -- | -- | case1 | G1 | GD1 | 6 months | ... | ... |
| Set8 | -- | -- | case1 | G1 | GD1 | 6 months | ... | ... |
| Set9 | -- | -- | case2 | G1 | GD1 | 6 months | ... | ... |
| Set10 | -- | -- | case2 | G2 | GD2 | 12 months | ... | ... |
| -- | DM1 | -- | case3 | G2 | GD2 | 12 months | ... | ... |
| -- | DM2 | -- | case3 | G2 | GD2 | 12 months | ... | ... |
| ... | ... | ... | ... | ... | | ... | ... | ... |
| ... | ... | ... | ... | ... | | ... | ... | ... |
| ... | ... | ... | ... | ... | | ... | ... | ... |
| ... | ... | ... | ... | ... | | ... | ... | ... |
| ... | ... | ... | ... | ... | | ... | ... | ... |

FIG. 6

| INSTRUMENT ID | SET ID | DELIVERY DATE AND TIME | REPAIR WORK | USER ID | WORK DATE ANT TIME | SENT-OUT DATE AND TIME | REPAIR FACTOR | COST |
|---|---|---|---|---|---|---|---|---|
| BM1 | | 2017/3/15 9:51:50 | Polishing | ... | 2017/3/17 10:51:50 | 2017/3/18 9:51:50 | Damaged cutting edge | ... |
| BM2 | | 2017/3/15 9:53:00 | Adjustment | ... | 2017/3/17 10:51:55 | 2017/3/18 9:55:50 | Unsmooth movement | ... |
| BM4 | | 2017/3/15 9:54:00 | Chip replacement | A123456 | 2017/3/17 10:51:40 | 2017/3/19 13:53:50 | Chip wear | ... |
| BOM1 | set1 | 2017/3/15 9:55:00 | Inspection | ... | 2017/3/18 11:55:00 | 2017/3/20 13:55:00 | ... | ... |
| BOM2 | set1 | 2017/3/15 9:55:00 | Inspection | ... | 2017/3/18 11:55:00 | 2017/3/20 13:55:00 | ... | ... |
| BOM3 | set1 | 2017/3/15 9:55:00 | Inspection | ... | 2017/3/18 11:55:00 | 2017/3/20 13:55:00 | ... | ... |
| BOM4 | set1 | 2017/3/15 9:55:00 | Inspection | ... | 2017/3/18 11:55:00 | 2017/3/20 13:55:00 | ... | ... |
| BOM5 | set1 | 2017/3/15 9:55:00 | Inspection | ... | 2017/3/18 11:55:00 | 2017/3/20 13:55:00 | ... | ... |
| ... | ... | ... | ... | ... | ... | ... | ... | ... |
| ... | ... | ... | ... | ... | ... | ... | ... | ... |
| ... | ... | ... | ... | ... | ... | ... | ... | ... |
| ... | ... | ... | ... | ... | ... | ... | ... | ... |
| ... | ... | ... | ... | ... | ... | ... | ... | ... |

FIG.7

| INSTRUMENT ID | AREA | USER ID | DELIVERY DATE AND TIME | WORK DATE AND TIME | SENT-OUT DATE AND TIME | PACKAGING | STERILIZATION | EFFECTIVE PERIOD |
|---|---|---|---|---|---|---|---|---|
| BM1 | A6 (Storage) | ... | ... | 2017/3/15 9:51:50 | ... | E1 | G1 | 6 months |
| BM1 | A1 (Surgical Operation) | ... | ... | 2017/5/11 15:51:00 | ... | --- | --- | --- |
| BM1 | A2 (Collection) | A123456 | ... | 2017/5/11 19:53:02 | ... | --- | --- | --- |
| BM1 | A3 (Cleaning) | ... | ... | 2017/5/11 20:31:50 | ... | --- | --- | --- |
| BM1 | A4 (Assembling) | ... | ... | 2017/5/12 9:11:50 | ... | E1 | G1 | 6 months |
| BM1 | A5 (Sterilization) | ... | ... | 2017/5/13 19:51:50 | ... | E1 | G1 | 6 months |
| BM1 | A6 (Storage) | ... | ... | 2017/5/14 10:41:50 | ... | --- | --- | --- |
| BM1 | A1 (Surgical Operation) | ... | ... | 2017/8/15 19:51:50 | ... | --- | --- | --- |
| BM1 | A2 (Collection) | ... | ... | 2017/8/16 9:51:50 | ... | --- | --- | --- |
| BM1 | A3 (Cleaning) | ... | ... | ... | ... | --- | --- | --- |
| BM1 | A7 (Repair) | A123457 | 2017/8/20 9:55:00 | ... | ... | E1 | --- | --- |
| BM1 | A4 (Assembling) | ... | ... | ... | ... | E1 | G1 | 6 months |
| BM1 | A5 (Sterilization) | ... | ... | ... | 2017/9/11 8:51:00 | E1 | G1 | 6 months |
| BM1 | A6 (Storage) | ... | ... | ... | ... | ... | ... | ... |
| BM1 | A1 (Surgical Operation) | ... | ... | ... | ... | ... | ... | ... |
| ... | ... | ... | ... | ... | ... | ... | ... | ... |

SURGICAL INSTRUMENT SET AND INSTRUMENT MANAGEMENT SYSTEM

CROSS REFERENCE TO RELATED APPLICATION

This application claims the benefit of priority to Japanese Patent Application No. 2018-144919 filed on Aug. 1, 2018. The entire contents of this application are hereby incorporated herein by reference.

BACKGROUND OF THE INVENTION

1. Field of the Invention

The present invention relates to a management system for surgical instrument sets and instruments.

2. Description of the Related Art

JP 2003-016198 A discloses a device that provides identification codes individually for small instruments used in medical consultation, surgical operation, and medical examination, and that reads the identification codes. Data about patients, data about doctors attending to the patients, inventory data of small steel instruments, and the like are stored as medical data in a database of the managing device. After a medical practice such as a surgical operation and a treatment is carried out for a patient, read data are compared with the medical data stored in the database of the managing device.

JP 2009-72338 A discloses a management system for a medical device that is cleaned after every one use for repeated use. JP 2009-72338 A discloses that a display part displays different colors according to the state of an endoscope.

JP 2012-215990 A discloses a device for supporting a picking work of medical instruments and materials. Specifically, the device includes a storage part that stores identifiers of medical instruments and materials and images of the medical instruments and materials, and another storage part that associates identifiers of mutually similar medical instruments and materials with each other and stores them. The device disclosed in JP 2012-215990 is configured or programmed to be able to display an image of a medical instrument or material specified by the user and an image of medical instrument or material that is similar the specified medical instrument or material side by side.

JP 2013-116234 A discloses an apparatus that manages the locations of medical devices. The apparatus disclosed in JP 2013-116234 A has a device information acquisition part that acquires device information including read information of identification tags attached to the medical devices from tag readers installed at a plurality of locations in a medical facility. A status holding part holds the statuses of the medical devices, which includes the locations of the medical devices that are identified by the acquired device information. A display control part causes a display device to display the statuses of the medical devices held by the status holding part. The display control part also causes the display device to hide the medical device in use for a medical practice among the medical devices.

JP 2015-197735 A discloses a device capable of distributing guidance information that helps general medical staff. The device disclosed therein uses medical work information that represents details of medical practices carried out by experienced medical staff as the guidance information. Then, the device distributes the guidance information in response to a request from general medical staff.

Japanese Registered Utility Model No. 3199614 discloses a surgical instrument management system. The system disclosed therein records photographs of external appearance related to surgical instruments. The system uses bar code information to create an asset number list of the surgical instruments prepared before a surgical operation. Next, the system reads identification patterns of the surgical instruments that were collected after the surgical operation. The system displays the external appearance photographs of the surgical instruments, and also determines whether or not the asset numbers of the surgical instruments collected after the surgical operation match the asset numbers of the surgical instruments prepared before the surgical operation.

SUMMARY OF THE INVENTION

Generally, surgical instruments are managed after a surgical operation in the following sequence; collection, cleaning, assembling, sealing, sterilization, and storage. The instruments are sterilized and thereafter stored, and used again in another surgical operation. Medical facilities, such as hospitals, possess many types of instruments and surgical instrument sets, and they store a plurality of instruments and surgical instrument sets of each type. When in use, the stored instruments or surgical instrument sets are picked out each time. Furthermore, instruments and surgical instrument sets may suffer various damages resulting from use, such as damaged cutting edges and partial smoothness in their joints, engagements, and moving parts of the instruments such as forceps. In such cases, the instruments and the surgical instrument sets are sent to outside contractors for repair. It is often the case that processing of instruments and surgical instrument sets is outsourced to outside contractors even when there are many instruments of the same type or many surgical instrument sets of the same type. When this is the case, management of the instruments and the surgical instrument sets is extremely complicated and troublesome.

A surgical instrument set and instrument management system proposed in this disclosure includes a first memory, a second memory, a third memory, and a fourth memory. The first memory is provided to store instrument IDs associated in a one-to-one correspondence with instruments. The second memory is provided to store set IDs associated in a one-to-one correspondence with surgical instrument sets each including a plurality of instruments. The third memory is provided to store work histories of the instruments each identified by a respective one of the instrument IDs, each of the work histories stored in association with the respective one of the instrument IDs and including work information about repair work. The fourth memory is provided to store work histories of the surgical instrument sets each identified by a respective one of the set IDs, each of the work histories stored in association with the respective one of the set IDs and including work information about repair work.

The preferred embodiments of the surgical instrument set and instrument management systems described herein are capable of management of surgical instruments and surgical instrument sets, including repairs to the instruments and surgical instrument sets.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 3 is a view illustrating an example of the configuration of a database 400 in which a first memory 101 and a second memory 102 are integrated into a single memory or storage.

FIG. 4 is a view illustrating a table 420 that records work information for a collection area A2.

FIG. 5 is a view illustrating a table 440 that records work information for a sterilization area A5.

FIG. 6 is a view illustrating a table 460 that records work information for a repair area A7.

FIG. 7 is a view illustrating an example of a table containing data obtained by extracting the work history of an instrument.

DETAILED DESCRIPTION OF THE PREFERRED EMBODIMENTS

Figure 1:
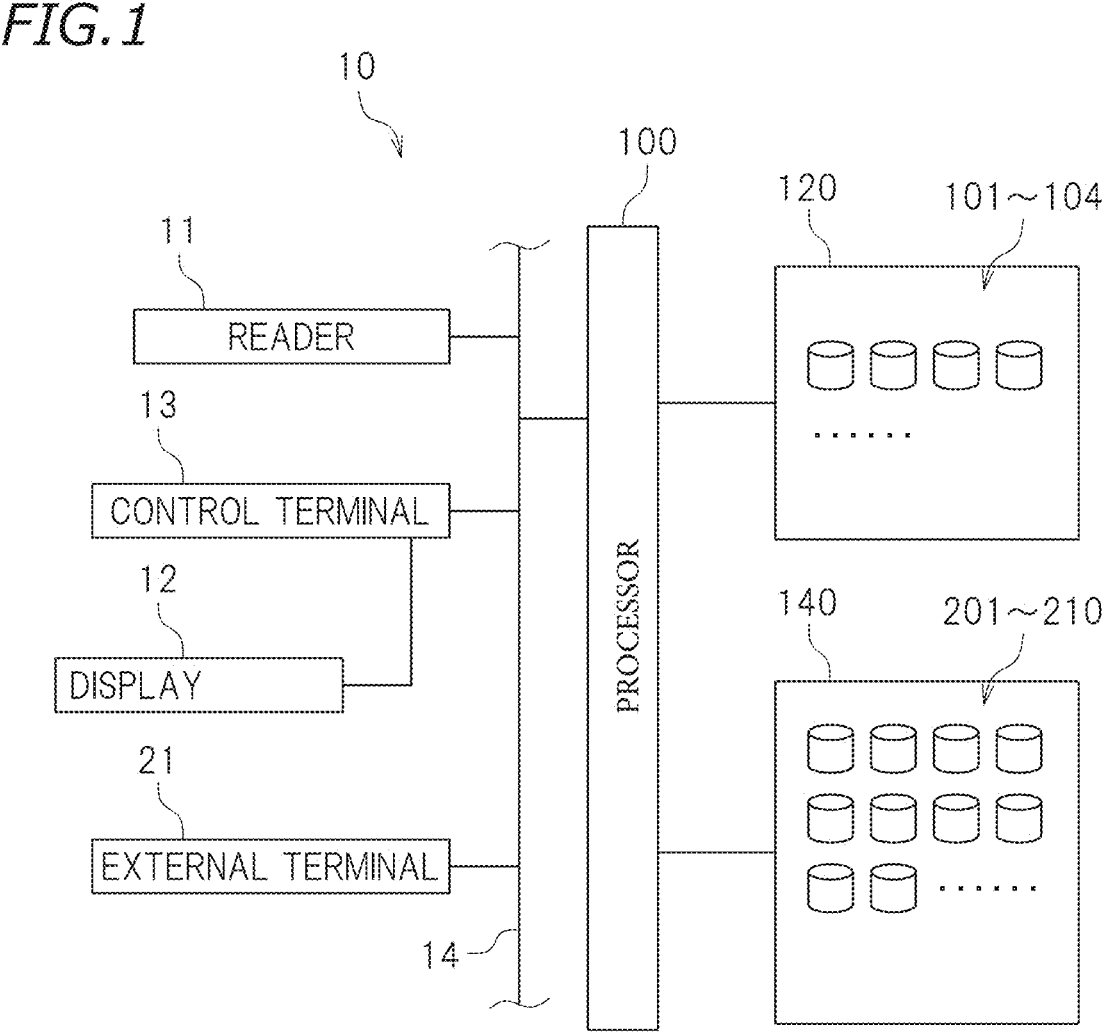
FIG. 1 is a schematic view illustrating a surgical instrument set and instrument management system 10.

Hereinbelow, surgical instrument set and instrument management systems according to preferred embodiments of the present invention will be described with reference to the drawings. It should be noted, however, that the preferred embodiments described herein are, of course, not intended to limit the present invention.

Herein, a surgical instrument set refers to a set of a plurality of medical instruments that are used in a surgical operation or in one of the steps of the surgical operation. Herein, the medical instruments may be referred to simply as "instruments", as appropriate.

Examples of the instruments of the surgical instrument set include trocars, forceps, cutting devices, cleaning and suction devices, scissors (Cooper scissors), scalpels, scalpel holders, cannulae, thumb forceps, retractors, scales, sounds, elevators, raspatories, suction tubes, rib spreaders, rib contractors, needle holders, injection syringes, metal basins, pus basins, glasses, pins, mirrors, files, mouth gags, wound clips, handpieces, chisels, sharp spoons, dissectors, surgical needles, intervertebral disc rongeurs, water receivers, needles, depressors, bougies, ventilation tubes, bone impactors, Luer bone rongeurs, needle-nose pliers, hammers, goniometers, pipettes, enemators, and syringes.

The medical instruments may include an instrument including a plurality of component parts. For example, the instruments used in a laparoscopic surgery, such as trocars, forceps, a cutting device, and a cleaning and suction device, are composed of a plurality of component parts, and they are collected after the surgical operation and disassembled into a plurality of component parts. Herein, a part that makes up a medical instrument is referred to as a "component part". Moreover, each component part may further include a plurality of component parts. When this is the case, each of the component parts may also be referred to as a "component part".

For the medical instruments and the component parts of the medical instruments, different cleaning procedures are specified. For this reason, the medical instruments and the component parts of the instruments are collected after a surgical operation, then sorted by specified cleaning procedures, and then sent to a cleaning step. After the cleaning, the instruments each including a plurality of component parts are assembled. Also, the medical instruments are classified by the type of surgical instrument set or by the type of medical instrument, and they are enclosed and sealed in predetermined containers. Thereafter, the instruments are sterilized in a specified sterilization method, and then stored until they are used next time. Thus, when in use, a surgical instrument set repeatedly undergoes the following cycle of steps: surgical operation→collection (sorting)→cleaning→assembling (sealing)→sterilization→storage→surgical operation. After a surgical operation, surgical instruments and surgical instrument sets undergo the following steps: collection, cleaning, assembling, sealing, sterilization, and storage. For this reason, many hospitals possess many types of surgical instrument sets and surgical instruments, and they store a plurality of surgical instrument sets and surgical instruments. When in use, the stored surgical instrument sets and surgical instruments are picked out each time.

When some problems are found in surgical instrument sets and surgical instruments, such as blunt blades due to damaged cutting edges, unsmooth engaging movements of forceps, and the like, such surgical instrument sets and surgical instruments may be sent out for repair in some cases. In other cases, such surgical instrument sets and the surgical instruments are sent out for regular inspections, so that necessary processing can be performed. Such repairs and inspections are carried out by specialist contractors outside hospitals. The instruments and the surgical instrument sets that are sent to specialist contractors are out of the normal cycle, which includes a surgical operation, collection, cleaning, sealing, sterilization, and storage. The information on the repairs and inspections is not managed together with the information of the instruments and the surgical instrument sets.

The surgical instrument set and instrument management system proposed herein may be used to manage instruments and surgical instrument sets, including, for example, those that are sent out to outside specialist contractors for repairs and inspections, appropriately and efficiently.

FIG. 1 is a schematic view of a surgical instrument set and instrument management system 10 (which may be simply referred to as a "system 10" when appropriate in this description). In the preferred embodiment shown in FIG. 1, the system 10 includes a reader 11, a display 12, a control terminal 13, and a processor 100, as the hardware configuration. However, the hardware configuration of the system 10 may not necessarily be limited to the preferred embodiment shown in FIG. 1. Various processes of the system 10 may be implemented by cooperative combinations of software and hardware in the control terminal 13 and the processor 100, for example.

As illustrated in FIG. 1, the system 10 proposed herein includes a first memory 101 to a fourth memory 104 and a first processor 201 to a tenth processor 210. Other than the first memory 101 to the fourth memory 104 and the first processor 201 to the tenth processor 210 as will be described herein, the system may include any additional memory or storage and/or any additional processor as required.

Among these components, the first memory 101 is provided to store instrument IDs associated in a one-to-one correspondence with instruments.

The second memory 102 is provided to store set IDs associated in a one-to-one correspondence with surgical instrument sets each including a plurality of instruments.

The third memory 103 is provided to store work histories of the instruments each identified by a respective one of the instrument IDs, each of the work histories stored in association with the respective one of the instrument IDs and including work information about repair work.

The fourth memory 104 is provided to store work histories of the surgical instrument sets each identified by a respective one of the set IDs, each of the work histories stored in association with the respective one of the set IDs and including work information about repair work.

The system 10 is able to obtain the work information about the repair work performed on the instruments and the surgical instrument sets.

The system 10 suitably records the work history of the instrument identified by an instrument ID and the work history of the surgical instrument set identified by a set ID in each of the steps of the following cycle: surgical operation→collection (sorting)→cleaning→assembling (sealing)→sterilization→storage→surgical operation, for example. The system 10 is further configured so that the work history of each of the instruments and the surgical instrument sets may include work information about repair work when appropriate. Hereinafter, an example of an application of the system 10 will be illustrated.

Areas A1 to A7

Figure 2:
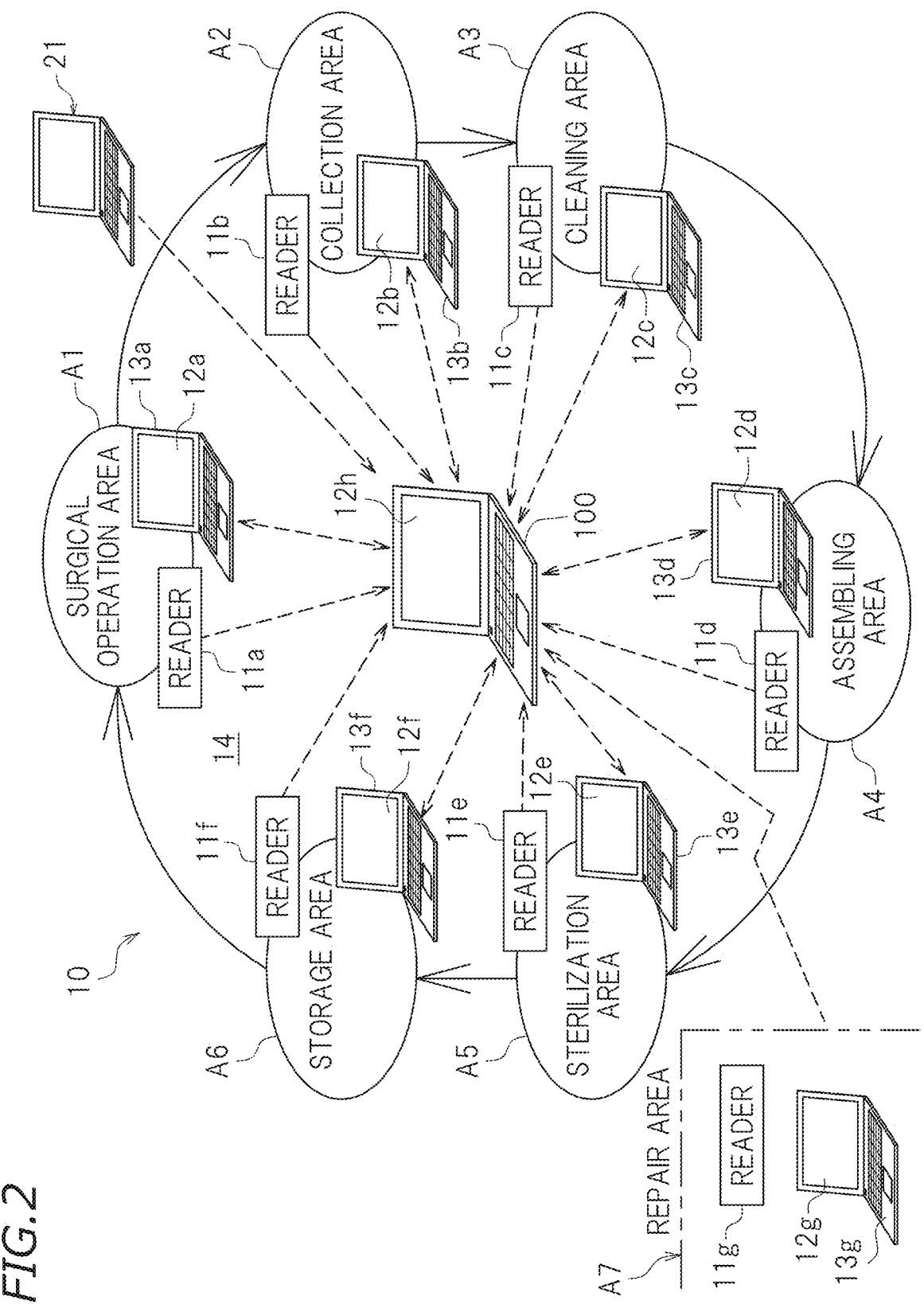
FIG. 2 is a schematic view illustrating an example of an application of the system 10.

FIG. 2 is a schematic view illustrating an example of an application of the system 10. The preferred embodiment shown in FIG. 2 includes separate areas A1 to A7, namely, a surgical operation area A1, a collection area A2, a cleaning area A3, an assembling area A4, a sterilization area A5, a storage area A6, and a repair area A7.

In the system 10, identifiers, which may also be referred to as "area IDs", are assigned in associated with the respective areas A1 to A7. The area IDs are stored in the master data in association with the respective areas A1 to A7.

The surgical operation area A1 is an area in which the instruments and the surgical instrument sets are used by doctors and nurses, and an area in which a surgical operation and a medical examination are carried out.

The collection area A2 is an area in which the surgical instrument sets and the surgical instruments are collected from the surgical operation area A1. Here, the surgical instruments may be collected separately, surgical instrument by surgical instrument.

The cleaning area A3 is an area in which the surgical instrument sets and the surgical instruments are cleaned. Here, the surgical instruments may be disassembled into components for cleaning.

The assembling area A4 is an area in which the cleaned surgical instrument sets and the cleaned surgical instruments are assembled and packaged into predetermined containers or bags.

The sterilization area A5 is an area in which the surgical instrument sets and the surgical instruments are sterilized. The surgical instrument sets and the surgical instruments are sterilized as they are kept packaged in predetermined containers or bags.

The storage area A6 is an area in which the sterilized surgical instrument sets and the sterilized surgical instruments are stored.

The repair area A7 is an area in which the instruments and the surgical instrument sets are repaired or inspected.

The work carried out in the repair area A7 is not limited to repairs, but may include maintenance work, such as inspections. Thus, when an instrument or a surgical instrument set is sent out for repair or inspection, the system 10 does not make a distinction between repair and inspection, but classifies the status of the instrument or the surgical instrument set into the concept of repair area.

Note that this preferred embodiment includes the surgical operation area A1, the collection area A2, the cleaning area A3, the assembling area A4, the sterilization area A5, the storage area A6, and the repair area A7, but this is merely illustrative.

Each of the above-described areas A1 to A7 can be defined as a location where a predetermined work is performed, but each of the areas A1 to A7 does not always match the location where a predetermined work is performed.

For example, the work processes such as cleaning, assembling, sterilization, and repair (repair and inspection) may be carried out by a specialist contractor, unlike surgical operations. In such cases, the cleaning area A3, the assembling area A4, the sterilization area A5, and the repair area A7 may be provided in a different facility from the facility that contains the surgical operation area A1, the collection area A2, and the storage area A6. It is also possible that the surgical operation area A1, the collection area A2, and the storage area A6 may be provided in different locations.

The system 10 is able to collectively manage the surgical instrument sets and the instruments that are used in a plurality of hospitals. In such cases, the areas A1 to A7 may be provided in each of the plurality of hospitals. Thus, each of the areas A1 to A7 is not limited to a single location.

In particular, the repair work may in some cases be carried out at a location outside a hospital. For example, instruments and surgical instrument sets may suffer various damages resulting from use, such as damaged cutting edges and partial smoothness in their joints, engagements, and moving parts of the instruments such as forceps. In such cases, the repair is outsourced to outside contractors.

In the preferred embodiment shown in FIG. 2, the repair area A7 is set to be a single area, but the location where the repair area A7 is set is not limited to a single location. In reality, it is possible that the outsourced contractors may be different depending on the type of work, such as repair and inspection.

In this preferred embodiment, as illustrated in FIG. 2, the readers 11a to 11g, each defining and functioning as a reading device, and the control terminals 13a to 13g are arranged respectively in the areas A1 to A7, In the system 10, the readers 11a to 11g and the control terminals 13a to 13g, which are disposed in the respective areas A1 to A7, may be associated respectively with the areas A1 to A7. For example, the system 10 may be configured or programmed so that the information that is input with the readers 11a to 11g or with the control terminals 13a to 13g may be recorded as the information that is input at the respective areas A1 to A7 in association with the IDs assigned to the respective areas A1 to A7.

System 10

As illustrated in FIG. 2, the system 10 is implemented by the processor 100, the control terminals 13a to 13g, and the readers 11a to 11g. The control terminals 13a to 13g and the readers 11a to 11g are disposed respectively in the areas A1 to A7. The control terminals 13a to 13g and the processor 100 respectively include displays 12a to 12h. In the present description, the reader(s), the display(s), and the control terminal(s) may be simply and collectively referred to as the "reader 11", the "display 12", and the "control terminal 13" when it is unnecessary to make a distinction between the readers 11a to 11g, between the displays 12a to 12h, and between the control terminals 13a to 13g.

Reader 11

Each of the readers 11a to 11g disposed in the respective areas A1 to A7 is a device that reads an item-identifying information symbol incorporated in each instrument of surgical instrument sets, an item-identifying information symbol incorporated in each component part of each instrument, or an item-identifying information symbol affixed to a bag or a container that encloses instruments or surgical instrument sets.

Item-Identifying Information

Here, the item-identifying information may be a two-dimensional symbol in a predetermined form. Examples of the item-identifying information used for the instruments in a surgical instrument set may include two-dimensional bar codes, contactless tags such as RFIDs, and engraved marks on the instrument surfaces. The engraved marks may be formed by laser engraving or impact engraving, for example.

Formation of the two-dimensional symbol by impact engraving may be performed by using an impact printer (e.g., MPX-95 manufactured by Roland DG Corp.), for example. Such an impact printer is capable of forming a data matrix with a very small size of, for example, about 1 mm square to about 4 mm square. The impact-engraved two-dimensional symbol is formed by indenting the surface of the instrument. The impact-engraved two-dimensional symbol is unlikely to damage, for example, a plated coating film on the surface of the instrument, so the impact-engraved two-dimensional symbol does not cause the instrument to rust easily. Moreover, due to the development of impact printer or the like, impact engraving of two-dimensional symbols can be applied to the existing instruments on which no two-dimensional symbol has been formed, and two-dimensional symbols can be set by the user and formed on the existing instruments.

In the assembling area A4, the sterilization area A5, or the storage area A6, each of the instruments is individually packaged appropriately, and each of the surgical instrument sets is collectively enclosed in a bag or a container, for example. In this case, each of the bags or the containers for enclosing an instrument or a surgical instrument set may be provided with item-identifying information, such as a two-dimensional symbol.

Each of the readers 11a to 11g may include a reader or sensor to detect the two-dimensional symbol. Examples of the reader or sensor to detect the two-dimensional symbol include cameras and CCD image sensors. The item-identifying information assigned to each instrument or each component part can be read by directing the item-identifying information symbol (which may be an impact-engraved two-dimensional symbol, for example) attached to each instrument or each component part toward the reader or sensor of one of the readers 11a to 11g. When the instrument or the surgical instrument set is enclosed in a bag or a container, the item-identifying information can be read by directing the item-identifying information attached on the bag or the container toward a desired one of the readers 11a to 11g.

Control Terminal 13 and Processor 100

Although each of the control terminals 13a to 13g and the processor 100 is depicted as a laptop terminal in FIG. 2, the type of terminal is not limited thereto. Each of the terminals may be a tablet computer or a desktop type computer, for example.

The control terminals 13a to 13g may be configured or programmed to cooperate with the processor 100 to implement various processes of the system 10. In this preferred embodiment, the processor 100 may be configured or programmed to function as a host computer that defines and functions as a backbone of the processes of the system 10. Each of the control terminals 13a to 13g may cooperate with the processor 100 and function as a client computer of the system 10. The processor 100 and the control terminals 13a to 13g include memory storage devices, and the memory storage devices of the processor 100 and the control terminals 13a to 13g may be connected to each other via a communication network 14. The memory storage devices of the processor 100 and the control terminals 13a to 13g may be configured so that information can be written into and retrieved from the memory storage devices.

Each of the control terminals 13a to 13g and the processor 100 includes an arithmetic device [also referred to as a processor, CPU (central processing unit), or MPU (microprocessing unit)] and a memory storage device (such as a memory and a hard disk). The functions of the control terminals 13a to 13g and the processor 100 are embodied by cooperative combinations with software stored in the memory storage device. For example, the configurations and the processes of the control terminals 13a to 13g and the processor 100 may be embodied as processing modules that perform predetermined computing tasks, data, or part thereof. Specifically, each of the processing modules is a program.

Referring to FIG. 1, each of the processor 100 and the control terminals 13a to 13g includes a memory storage area 120 for storage of data and a memory storage area 140 for storage of processing modules.

The memory storage area 120 for storage of data stores various kinds of master data and various data acquired by the readers 11a to 11g and the control terminals 13a to 13g, in addition to the above-described memories 101 to 105.

The memory storage area 140 for storage of processing modules stores processing modules of the system 10 as appropriate. The processing modules stored in the memory storage area 140 are not limited to the foregoing processors 201 to 210. The processor 100 and the control terminals 13a to 13g may be configured or programmed to, for example, call and execute the processing modules stored in the memory storage area 140. Herein, the memory storage area 120 that stores data may be constructed by, for example, a separate data server that is independent of the processor 100 and the control terminals 13a to 13g.

Each of the control terminals 13a to 13g and the processor 100 may be embodied by a single device, or may exhibit the functions as a processor by cooperative combinations of a plurality of devices. That is, although FIG. 1 depicts that the processor 100 is including one single device, the processor 100 is not limited to being one single device.

The control terminals 13a to 13g and the processor 100 respectively include displays 12a to 12h, each of which functions as a display. The displays 12a to 12h are configured or programmed to display images according to programs incorporated in the control terminals 13a to 13g and the processor 100. Each of the displays 12a to 12h may be including a touchscreen. When each of the displays 12a to 12h includes a touchscreen, the system 10 may be configured or programmed to be operated by the user's touching the screen of the display 12, for example.

The readers 11a to 11g, the control terminals 13a to 13g, and the processor 100 may be bidirectionally date-communicably connected to each other. In the preferred embodiment shown in FIG. 2, the readers 11a to 11g, the control terminals 13a to 13g, and the processor 100 are cooperated with each other in such a state as to be capable of making data communication with each other through the communication network 14. The control terminals 13a to 13g, the readers 11a to 11g, and the processor 100 may be connected in such a state as to be able to make information communication with each other via, for example, a wireless communication network through a router (not shown) or a wired communication network through LAN cables.

Display 12

Each of the displays 12a to 12g of the control terminals 13a to 13g as well as the display 12h of the processor 100, which are shown in FIG. 2, functions as the display 12 shown in FIG. 1. In the preferred embodiment shown in FIG. 2, the control terminals 13a to 13g and the processor 100 are cooperated with each other to function as the processor 100 of the system 10 (see FIG. 1). In the preferred embodiments shown in FIGS. 1 and 2, the system 10 is embodied by a plurality of devices. In the system 10, a plurality of personal computers, such as the control terminals 13a to 13g and the processor 100, cooperate with each other. The system 10 may be used simultaneously in parallel at a plurality of remote locations by a plurality of different users. A large number of surgical instrument sets and a large number of instruments may be managed in parallel in a plurality of steps.

Arrangement of Reader 11, Etc.

FIG. 2 shows that one reader 11, one display 12, and one control terminal 13 are arranged in each of the areas A1 to A7. However, the arrangement of the reader 11, the display 12, and the control terminal 13 is not limited to the preferred embodiment shown in FIG. 2.

It is possible that the actual locations of the areas A1 to A7 may be overlapped with each other. For example, when collection is carried out at the same location as where a surgical operation or a medical practice is carried out, the location of the surgical operation area A1 and the location of the collection area A2 may be overlapped with each other. In this case, it is also possible that the reader 11, the display 12, and the control terminal 13 may be used in common between the surgical operation area A1 and the collection area A2. In addition, it is possible that the functions and settings of the control terminal 13 may be switched from one to another so as to be suitable for the areas A1 to A7 by, for example, a process on software. For example, the control terminal 13 may be configured or programmed to be able to switch between the functions and settings suitable for the surgical operation area A1 and the functions and settings suitable for the collection area A2, as appropriate, by a predetermined operation.

The system 10 may further include further larger numbers of readers 11, displays 12, and control terminals 13. On the contrary, the reader 11, the display 12, and the control terminal 13 may not be arranged in all of the areas A1 to A7. It is also possible that different areas among the areas A1 to A7 may share a reader 11, a display 12, and a control terminal 13.

For example, in a small-scale hospital, the cycle of surgical operation→collection (sorting)→cleaning→assembling (sealing)→sterilization→storage is performed in a limited space. In such cases, various types of functions performed by the readers 11a to 11g, the control terminals 13a to 13f, and the processor 100 may be aggregated into a single reader and a single control terminal. Thus, the system 10 may be configured as a stand-alone apparatus. On the other hand, in a large-scale hospital that has a large number of operating rooms, the system may be configured so that the processor 100 is connected bidirectionally communicatively with the control terminals 13 in the respective areas. In this case, the system 10 may be built as a client-server system in which the processor 100 defines and functions as a host server and each of the control terminals 13 of the respective areas defines and functions as a client. Alternatively, the system 10 may be built as a cloud-based system operated in a plurality of hospitals and facilities that are remote from each other. In this case, the system 10 may be built as such a system that, for example, the processor 100 defines and functions as a data center in which various types of data are aggregated, and various types of functions of the system 10 are usable from control terminals 13 arranged in a plurality of remote hospitals and facilities through, for example, a web browser.

In the preferred embodiment shown in FIG. 2, the reader 11a and the control terminal 13a are preferably provided in the surgical operation area A1. However, the reader 11a and the control terminal 13a may not be provided in the surgical operation area A1. For example, as long as the storage area A6 and the collection area A2 are provided with the readers 11b and 11f and the control terminals 13b and 13f, the surgical operation area A1 need not be provided with the reader 11a or the control terminal 13a. In this case, the work information at the surgical operation area A1 may be input at the storage area A6 and the collection area A2.

Some processes such as cleaning work, assembling work, sterilization work, and repair work may be carried out by a specialist contractor outside the hospital. It is possible that such an outside contractor is not involved in the system 10. This means that some areas such as the cleaning area A3, the assembling area A4, the sterilization area A5, and the repair area A7 may not be provided with the reader 11, the display 12, or the control terminal 13. Among them, the cleaning area A3, the assembling area A4, and the sterilization area A5 are within the normal use cycle, surgical operation→collection (sorting)→cleaning→assembling (sealing)→sterilization→storage. This means that these work processes are performed regularly, so the contents and the costs are foreseeable.

On the other hand, the repair work, such as repairing of instruments and surgical instrument sets, is out of the normal use cycle, surgical operation→collection (sorting)→cleaning→assembling (sealing)→sterilization→storage, and it can occur irregularly or unexpectedly. Therefore, the contents and the costs of the repair work are difficult to foresee.

For the repair work, surgical instrument sets and instruments are sent from the collection area A2 and the assembling area A4, for example, for repair and inspection.

It is possible that the repair area A7 may be set in an outside specialist contractor and the repair area A7 may not be provided with the reader 11 or the control terminal 13. Accordingly, regardless of the preferred embodiment shown in FIG. 2, the repair area A7 may not be provided with the reader 11g or the control terminal 13g.

For example, instruments and surgical instrument sets are sent to the repair area A7 from another area. Then, when the work to be performed at the repair area A7 is completed, the instruments and the surgical instrument sets are returned from the repair area A7 to the other area. This means that, if the other area is provided with a reader 11 and a control terminal 13, it is possible to manage the information about sending of surgical instrument sets and instruments to the repair area A7 and the information about The information about the work contents performed at the repair area A7 can be input at the area from which the instruments and the surgical instrument sets are sent out, or at the area to which the instruments and the surgical instrument sets are returned. For inputting the work information, this also applies to the case where the work processes to be performed at the cleaning area A3, the assembling area A4, and the sterilization area A5 are outsourced to outside contractors. Specifically, the work information may be input at the area to which the instruments and the surgical instrument sets are returned from the cleaning area A3, the assembling area A4, and the sterilization area A5.

Configuration of System 10

As illustrated in FIG. 1, the system 10 includes the first memory 101 to the fourth memory 104 and the first processor 201 to the tenth processor 210.

In the system 10, the processes to be performed by the processors may be processed by any of the processor 100 and the control terminals 13a to 13g. The information stored in the memories may be managed by the processor 100 as a host computer, for example, and may be shared by the control terminals 13a to 13g.

First Memory 101

The first memory 101 stores instrument IDs associated in a one-to-one correspondence with instruments. Specifically, in this system 10, the instruments of each of the surgical instrument set are provided with respective instrument IDs. Each of the instrument IDs corresponds in a one-to-one correspondence to a specific instrument. In this preferred embodiment, as mentioned above, each of the instruments is provided with item-identifying information that is readable by the readers 11a to 11g. The first memory 101 may store the item-identifying information assigned to each of the instruments and the instrument ID of each of the instruments in association with each other. The system 10 may be configured or programmed to be able to identify the instrument ID associated in a one-to-one correspondence with the instrument when the item-identifying information is read by one of the readers 11a to 11g.

In some cases, each of the instruments may further include a plurality of component parts. In the system 10, the component parts that constitute each of the instruments are also provided with parts IDs. Each of the parts IDs corresponds in a one-to-one correspondence to a specific instrument and a component part of the instrument. The system 10 is also able to identify the instruments of each of the surgical instrument sets and the component parts of each instrument with parts IDs. In this case, each of the component parts may be also provided with item-identifying information. The system 10 may also be configured or programmed so that, when the item-identifying information is read by one of the readers 11a to 11g, the system 10 can identify the parts ID and the instrument ID that are associated in a one-to-one correspondence with each of the component parts. Thus, each of the instruments and the parts is identified by causing the reader 11 to read the item-identifying information assigned to each of the instruments and the parts. Thus, the work information can be input correctly for each individual items of the instruments or component parts even when there are a plurality of instruments of the same type and a plurality of component parts of the same type.

Second Memory 102

The second memory 102 stores set IDs associated in a one-to-one correspondence with surgical instrument sets each including a plurality of instruments. That is, in this system 10, the surgical instrument sets are provided with set IDs that are associated in a one-to-one correspondence with the surgical instrument sets so that each of the surgical instrument sets can be identified by a set ID.

In this preferred embodiment, the set IDs are stored in such a manner that the set IDs associated in a one-to-one correspondence with the surgical instrument sets are further associated with the instrument IDs of the instruments that are included in the corresponding surgical instrument sets and also with the parts ID of the component parts that are included in the corresponding surgical instrument sets. That is, when a set ID is identified, it is possible to identify the instrument IDs of the instruments included in the surgical instrument set identified by the set ID as well as the parts IDs of the component parts included in the surgical instrument set identified by the set ID. On the other hand, when an instrument ID is identified, it is possible to identify the set ID of the surgical instrument set that includes the corresponding instrument.

In the case where an instrument includes component parts, the parts IDs of the component parts included in the instrument are identified from the instrument ID. Also, when a parts ID of a component part is identified, the instrument ID of the instrument that includes the component part is identified accordingly. Moreover, in the case where when the instrument is included in a surgical instrument set, it is possible to identify the set ID of the surgical instrument set that is associated with the parts ID when the parts ID of a component part is identified. For example, the second memory 102 may store the item-identifying information assigned to each instrument, instrument IDs, and set IDs in association with each other. The system 10 may be configured or programmed to be able to identify the instrument ID and the set ID when item-identifying information is read by one of the readers 11a to 11g. Furthermore, the system 10 may be configured or programmed to be able to identify the corresponding set ID when the item-identifying information assigned to a component part is read by one of the readers 11a to 11g.

The first memory 101 and the second memory 102 described above may be including respective independent databases. Alternatively, the first memory 101 and the second memory 102 may be including a single database. FIG. 3 is a view illustrating an example of the configuration of a database 400 in which the first memory 101 and the second memory 102 are integrated into a single unit. FIG. 3 shows that there are provided a column 401 that stores set IDs, a column 402 that stores surgical instrument set names; a column 403 that stores instrument IDs; a column 404 that stores instrument names; a column 405 that stores parts IDs; a column 406 that stores GS1 codes as item-identifying information; a column 407 that stores image files of surgical instrument sets, instruments, and component parts; and columns 408 and 409 that store information related to attributes of instruments and surgical instrument sets. These IDs and pieces of information are stored in association with each other. Each of the image files contains an image of a surgical instrument set, an instrument, or a component part. The system 10 can be configured or programmed to display the image files on the display 12 (see FIG. 1).

As in the preferred embodiment shown in FIG. 3, for the instruments included in the surgical instrument sets, the first memory 101 may additionally store set IDs of the surgical instrument sets respectively associated with the instrument IDs. As a result, when the instrument ID of an instrument included in a surgical instrument set is identified, the set ID of the surgical instrument set that includes the instrument is accordingly identified.

In addition, attribute information is stored in association with the instrument IDs and the set IDs. Herein, in cases of hospitals, for example, the attribute information may be specified as information for identifying a medical department, such as surgery and internal medicine. Moreover, when the instruments and the surgical instrument sets of a plurality of hospitals need to be managed collectively, the attribute information includes information for distinguishing one hospital from another. Thus, the attribute information may include a plurality of types of information at some hierarchical levels. For example, in this preferred embodiment, attribute 1 includes information indicating a hospital, and attribute 2 includes information indicating a medical department. The attribute information is not limited thereto, and may include different types of information other than hospitals and medical departments, such as the manufacturer and the model of the instrument or the surgical instrument set. Thus, the attribute information may be information for classifying instruments and surgical instrument sets.

As illustrated in FIG. 3, the system 10 may be provided with pre-stored master data, which include set IDs, instrument IDs, and parts IDs, as well as associated information therewith, such as item-identifying information, image data, and attribute information. The information that is stored in the master data is not limited to the items listed in FIG. 3.

For example, the pre-stored master data of the system 10 may also include user IDs for identifying workers, for example. The user IDs may be configured so that they can be identified by a two-dimensional code attached a name tag distributed to each of the workers, or by using biometric authentication of each individual worker. For example, the user IDs may be configured so that they can be identified by a type of information that is readable with the reader 11b. Each of the readers 11a to 11g, the control terminals 13a to 13g, and the processor 100 may also be provided with item-identifying information assigned thereto, which may also be stored in advance in the master data of the system 10.

Moreover, the pre-stored master data of the system 10 may also include information indicating cleaning methods, packaging materials used in sterilization and storage, sterilization methods, and the like, as appropriate.

Third Memory 103 and Fourth Memory 104

The third memory 103 is provided to store work histories of the instruments each identified by a respective one of the instrument IDs, each of the work histories stored in association with the respective one of the instrument IDs and including work information about repair work.

The fourth memory 104 is provided to store work histories of the surgical instrument sets each identified by a respective one of the set IDs, each of the work histories stored in association with the respective one of the set IDs and including work information about repair work.

Herein, the work information is information about various types of work, and it may contain information such as the date and time of the work, the content of the work, the worker, and the cost. For the work information, different items to be recorded and different formats are set for different types of work. Because the items and the formats are thus set, various items of work information that have been input at different work areas can be integrated in an appropriate manner.

The work history may be a data group in which items of work information are aggregated, and it may be data in which items of work information are aggregated in chronological order based on the date and time of the work.

In this preferred embodiment, the readers 11a to 11g are arranged respectively in the areas A1 to A7, each being a predetermined work space. Each of the instruments possesses item-identifying information. In the first memory 101, the item-identifying information, the instrument ID, and the set ID are stored in association with each other for each of the instruments. The work information of each instrument or each surgical instrument set may be input after the instrument or the surgical instrument set has been identified by reading the item-identifying information with one of the readers 11a to 11g.

Tenth Processor 210

In this preferred embodiment, the tenth processor 210 is configured or programmed to, if one of the instrument IDs is identified when the item-identifying information is identified by one of the readers, add information about work performed for one of the instruments identified by the one of the instrument IDs to the work history of the one of the instruments in association with the identified one of the instrument IDs. The tenth processor 210 is also configured to, if one of the set IDs is identified when the item-identifying information is identified by one of the readers, add information about work performed for one of the surgical instrument sets identified by the one of the set IDs to the work history of the one of the surgical instrument sets in association with the identified one of the set IDs. When the item-identifying information is detected by one of the readers 11a to 11g, this system 10 is able to identify an instrument ID and a set IDs from the item-identifying information. As a result, it is possible to identify an individual one of instruments or and surgical instrument sets even when there are instruments or surgical instrument sets of the same type.

As illustrated in FIG. 2, the system 10 includes the readers 11a to 11g arranged in the respective areas A1 to A7. When one of the readers 11a to 11g detects item-identifying information, an instrument ID is identified correspondingly by the item-identifying information. As a result, in the areas A1 to A7, the work information about the work performed for the corresponding instrument, the instrument ID of which is identified by the respective one of the readers 11a to 11g, is added to the work history of the instrument. Alternatively, when a set ID is identified by the item-identifying information, the information about the work performed for the corresponding surgical instrument set in the areas A1 to A7 is added to the work history of the surgical instrument set. Because an instrument or a surgical instrument set is identified in this way by using the readers 11a to 11g, inputting of the work history of the instrument or the surgical instrument set is carried out more reliably. In addition, the work history of an instrument or a surgical instrument set may record, for example, the time at which the item-identifying information is detected by one of the readers 11a to 11f, in addition to the information about the work. This serves to precisely record the time in the work history. Furthermore, it is also possible to add the information on the worker, the instruments and the materials used for the work, and the like, to the work history.

Herein, an example is shown that when item-identifying information is detected, a corresponding instrument ID is identified by the item-identifying information, and the information about the work performed for the instrument in the areas A1 to A7 is added to the work history of the instrument. However, specific methods of storing the work history of the instrument identified by an instrument ID in association with the instrument ID and specific methods of storing the work history of the surgical instrument set identified by a set ID in association with the set ID are not limited to the above-described preferred embodiment, unless specifically stated otherwise. For example, in the areas A1 to A7, the worker may manually input the work information or a portion of the work information by using the respective control terminals 13a to 13g.

Work Information for Surgical Operation Area A1

In the surgical operation area A1, for example, when a stored instrument or a stored surgical instrument set is brought into the surgical operation area A1, item-identifying information is detected by the reader 11a and the instrument ID or the set ID is identified. Then, the information indicating the date on which the instrument or the surgical instrument set is delivered and the information during use are recorded in association with the instrument ID or the set ID. The work information recorded at the surgical operation area A1 may include, for example, the users (workers) such as doctors, patients, medical record numbers of the patients, surgical operations, and consultation numbers. This enables the system 10 to store the work history indicating what kind of surgical operation the instrument or the surgical instrument set was used for. As a result, the amount of information that can be tracked by the work history of the instrument or the surgical instrument set increases. It is also possible that the system 10 may import information contained in an existing electronic patient record into the work information obtained at the surgical operation area A1. It is also possible that the instrument IDs or the set IDs of the instruments or the surgical instrument sets that have been used in a surgical operation may be written into the existing electronic patient record. Thus, it is possible to construct a system that the existing electronic patient record and the system 10 cooperate with each other.

Work Information for Collection area A2

The instruments and the surgical instrument sets used that were used in the surgical operation area A1 are brought into the collection area A2. In the collection area A2, the item-identifying information is detected by, for example, the reader 11b, and the instrument IDs and the set IDs are identified. The work information recorded at the collection area A2 may include information such as the date of collection and the worker ID, for example.

In the collection area A2, the display 12b may display a list of the instruments included in a surgical instrument set, for example. While the reader lib is detecting the item-identifying information of the instruments included in the surgical instrument set, the instruments may be collected. When the item-identifying information of the instruments included in the surgical instrument set is detected, the instruments can be identified on the display 12b. It is also possible that, when the worker specifies an instrument displayed on the display 12b in the collection work, the display 12b may dim the indication of the instrument for which the item-identifying information was detected from the list of the instruments included in the surgical instrument set. In this case, the display 12b may include a touchscreen. The display 12b may be configured or programmed so that, when the worker touches an indication representing the instrument to be collected (in other words, the instrument identified by the item-identifying information) from the list of the instruments displayed on the display 12b, the indication of the instrument is changed. By such a process, the worker may be allowed to easily recognize visually that the subject instrument has been collected properly. Then, when all the instruments included in the surgical instrument set used in the surgical operation area A1 have been collected in the collection area A2, the collection of the surgical instrument set is completed. At that time, it is possible that the worker may be allowed to easily recognize visually that the subject instruments have been collected properly by, for example, dimming the indication of the subject surgical instrument set or displaying an icon indicating the completion of collection on the display 12b.

Work Information for Cleaning Area A3

In the cleaning area A3, the instrument ID is identified when the item-identifying information of an instrument included in a surgical instrument set is detected by, for example, the reader 11c. The work information obtained at the cleaning area A3 may be stored in association with the identified instrument ID. The work information obtained at the cleaning area A3 may include, for example, a user ID and information on the cleaning method such as the cleaning machine and the detergent that are used for the cleaning.

It is also possible that the instrument ID and a cleaning method may be associated with each other and stored in advance in the system 10. In this case, it is possible that when the reader 11c detects the item-identifying information of an instrument included in a surgical instrument set, the display 12c in the cleaning area A3 may display a cleaning process required for the instrument on the screen based on the identified instrument ID. Because the instrument ID is identified by the reader 11c, it is unlikely that the cleaning process is performed for a wrong instrument or that the work information is input for a wrong instrument. The reader 11c may be provided for, for example, a cleaning machine. In that case, it is also possible that, while the reader 11c is reading the item-identifying information of the instrument, the instrument may be put into the cleaning machine. It is also possible that the information on the cleaning conditions and the like that are set for the cleaning machine may be recorded in the work information. Herein, examples of the cleaning method include manual cleaning, automated single-bath cleaning, automated multi-bath cleaning, ultrasonic cleaning, and chemical cleaning. Each of the cleaning methods may use a predetermined cleaning machine and a predetermined detergent in a predetermined way.

In addition, information contained in an existing electronic patient record may be imported into the work information obtained at the surgical operation area A1. In that case, the cleaning method and the sterilization method for the instrument may be recorded in the master data in advance, in association with information about patients and surgical operations. Accordingly, the system 10 may be constructed to appropriately identify a cleaning method required for the instrument based on the master data and the information about patients and surgical operations that is contained in the work information obtained at the surgical operation area A1. In this way, the system 10 may be constructed so as to identify a special cleaning method when such a special cleaning method is required by the instrument or the surgical instrument set based on the information provided by the electronic patient record. Likewise, in the sterilization area A5, the system 10 may be constructed so as to identify a special sterilization method when such a special sterilization method is required by the instrument or the surgical instrument set based on the information provided by the electronic patient record.

Work Information for Assembling Area A4

In the assembling area A4, various activities are performed, such as assembling of an instrument from cleaned parts, and collecting of instruments to be included in a surgical instrument set to form the surgical instrument set. In assembling the instrument, required lubricating oil may be applied to the instrument.

In the assembling area A4, when the item-identifying information of an instrument included in a surgical instrument set is detected by the reader 11d, for example, the instrument ID of the instrument and the set ID of the surgical instrument set are identified. Then, the list of the instruments included in the surgical instrument set is displayed. At this time, it is possible that the necessary assembling work that needs to be performed in the assembling area A4 may be displayed on the screen. For example, it is possible to display the lubricating oil to be applied at the time of assembling of the instrument when such is specified in advance.

Each of the instruments and the surgical instrument sets is enclosed in a predetermined bag or container. At that time, the packaging material and the packaging method may be recorded additionally. Examples of the packaging material include nonwoven fabric, sterilization bags, containers, and trays. Examples of the packaging method include wrapping the instrument or the surgical instrument set with nonwoven fabric, enclosing the instrument or the surgical instrument set in a sterilization bag, and enclosing the instrument or the surgical instrument set that is wrapped with nonwoven fabric in a sterilization bag. The surgical instrument set should be packaged while checking that all the instruments to be included in the surgical instrument set are present. In this case, it is possible that the instruments may be packaged while displaying the list of instruments to be included in the surgical instrument set on the display 12d displays and detecting the item-identifying information of the instruments with the reader 11d when packaging the instruments. Also, it is possible to change the indication of the instrument that has already been packaged in the list of the instruments. When the indication of the packaged instrument changes on the display 12d, the worker can easily confirm the instruments that have not yet been packaged. This prevents an instrument from missing from the surgical instrument set, and prevents a wrong instrument from being placed into the surgical instrument set.

The instruments and the surgical instrument sets are packaged, for example, in a bag or a container and hermetically sealed therein. The instruments that are not included in surgical instrument sets are packaged piece by piece independently. The surgical instrument set is packaged, for example, in a single collection of instruments. Each of the packaged bags or the packaged containers may be provided with item-identifying information that identifies the bag or the container. Then, the item-identifying information attached to the bag or the container may be stored in association with the instrument ID for identifying the instrument enclosed therein and the set ID for identifying the surgical instrument set enclosed therein. For example, in the packaging work, an instrument or a surgical instrument set is enclosed in a bag or a container while reading the individual item information attached on the bag or the container and the individual item information of the instrument or the surgical instrument set to be enclosed in the bag or the container. At this time, the system 10 may store the item-identifying information of the bag or the container in association with the item-identifying information of the instrument or the surgical instrument set that is enclosed therein. This makes it possible to identify the set ID of the surgical instrument set or the instrument ID of the instrument that is enclosed in the bag or the container in a post-process, based on the item-identifying information attached on the bag or the container.

Thus, in the assembling area A4, the work information obtained at the assembling area A4 is stored in association with the item-identifying information of the bag or the container, for example, which is read by the reader 11c. The work information obtained at the assembling area A4 may include the instrument ID of the instrument enclosed in a bag or a container, the set ID of the surgical instrument sets enclosed in a bag or a container, the date and time at which item-identifying information is read by the reader 11c in assembling work, and the user ID for identifying the worker. Moreover, it is possible that the item-identifying information of the bag or the container and the item-identifying information of the instrument or the surgical instrument set enclosed therein may be stored in association with each other.

Work Information for Sterilization Area A5

In the sterilization area A5, the instruments and the surgical instrument sets are kept enclosed in a packaging material, such as a bag or a container, while they are handled. In the sterilization area A5, the item-identifying information attached to the bag or the container is read by, for example, the reader 11e. Then, the instrument or the surgical instrument set is identified based on the item-identifying information. Then, a predetermined sterilization treatment is performed for the instrument or the surgical instrument.

In this preferred embodiment, a database is prepared in advance in which a sterilization treatment is pre-stored in association with the instrument ID or the set ID. In the sterilization area A5, the item-identifying information attached to the bag or the container is read by the reader 11e, and the instrument ID or the set ID of the instrument or the surgical instrument set that is enclosed in the bag or the container is identified. The system 10 may be configured so that, based on the instrument ID or the set ID, the sterilization treatment to be performed at the sterilization area A5 is specified and displayed on the display 12e.

This serves to allow the worker to easily understand the sterilization treatment that is to be performed for the instrument or the surgical instrument set enclosed in a bag or a container. In the sterilization area A5, the reader 11e may further be installed on a sterilizer, such as an autoclave. In that case, the instrument or the surgical instrument set may be placed into the sterilizer after the item-identifying information attached to the bag or the container is read by the reader 11e. This serves to allow the sterilization treatment to be performed under predetermined conditions (such as temperature and treatment time). In addition, the system 10 may be configured or programmed to prevent the worker from making errors by, for example, sounding an alarm in cases where the sterilizer in which the instrument or the surgical instrument set is to be placed is inappropriate or the conditions of the sterilization treatment that are set in the sterilizer are inappropriate when the item-identifying information attached to the bag or the container is read by the reader 11e.

In the sterilization area A5, the item-identifying information attached to the bag or the container is read by the reader 11e, for example. Then, the instrument ID or the set ID is identified in association with the item-identifying information attached to the bag or the container. Then, the work information obtained at the sterilization area A5 is stored in association with the instrument ID, the set ID, and the item-identifying information attached to the bag or the container. The work information obtained at the sterilization area A5 may include, for example, the sterilization method and conditions of the sterilization treatment. Specifically, the work information obtained at the sterilization area A5 may further include, for example, information indicating the sterilizer used for the sterilization treatment, conditions of the sterilization such as temperature and treatment time, the end date and time of the sterilization treatment, the worker, and the like.

Work Information for Storage Area A6

The storage area A6 stores the instruments and the surgical instrument sets after sterilization. In the storage area A6, the item-identifying information attached to each of the bags and the containers is read by the reader 11f. Then, the instrument ID or the set ID is identified in association with the item-identifying information attached to each of the bags and the containers. After the instrument IDs of the enclosed instruments and the set IDs of the enclosed surgical instrument sets are identified, the bags and the containers are sorted and stored in an appropriate location. The work information recorded at the storage area A6 may include, for example, information such as the storage location of each of the instruments and the surgical instrument sets and the date and time indicating when each of the instruments and the surgical instrument sets has been stored. Because the storage location of each of the instruments and the surgical instrument sets is recorded, it is easy to pick out the instrument or the surgical instrument set. Also, because the date and time when each of the instruments and the surgical instrument sets has been placed into storage is recorded, it is possible to calculate the period for which each of the instruments and the surgical instrument sets has been stored in the storage area A6.

Work Information for Repair Area A7

In the repair area A7, repairs and inspections are carried out for the instruments and the surgical instrument sets. In the repair area A7, the reader 11g identifies the item-identifying information of an instrument or a surgical instrument set to identify the instrument ID or the set ID. The work information recorded at the repair area A7 includes, for example, processes such as repairs and inspections that have been performed for the instruments and the surgical instrument sets, the date and time when the instruments and the surgical instrument sets have been brought in, and the date and time when the instruments and the surgical instrument sets have been sent out. It is also possible to record the content, date, and time of the work performed in the repair area A7. The work information may also include the information about a factor that necessitates repair work.

Here, the work information about repair work may record various factors that necessitates repair work, including, for example, damaged cutting edges of scalpels, improper engagement and non-smooth movement of forceps, and rust on instruments. Furthermore, the information that may be recorded as the causes of improper engagement of forceps and the like may include long-term use, excessive force, dropping, and plating peeling. These factors that have necessitated the repair work may be coded into appropriate data in the master data that have been prepared in advance. Furthermore, the work information about the repair work may include information about the cost required for the repair work. The information recorded as the cost required for the repair work may be, for example, the amount of cost billed by the contractor to which the repair work was outsourced.

In this case, when work contents and billing data are digitized by the contractor to which the repair work is outsourced, the system 10 may be configured or programmed to read the work contents and billing data as the work information about repair work. In addition, when unit prices of the cost required for the repair work are predetermined for each type of instrument, each type of surgical instrument set, or each type of work content, the predetermined unit prices may be stored in the master data. In this case, the system 10 may be configured or programmed such that, when an instrument ID, a set ID, or a wok content is identified, the cost required for the repair work is obtained accordingly.

It should be noted that, as already mentioned previously, the repair area A7 may not be provided with the reader 11g or the control terminal 13g. When this is the case, one of the readers 11a to 11f or one of the control terminals 13a to 13f, which are provided in other areas, may be configured or programmed to identify the instrument or the surgical instrument set and to record processes such as repairs and inspections that have been performed for the instruments and the surgical instrument sets, the date and time when the instruments and the surgical instrument sets have been brought in, and the date and time when the instruments and the surgical instrument sets have been sent out. These items of information may be input by the reader 11 or the control terminal 13 that is installed in a supplying area from which the instruments and the surgical instrument sets are sent to the repair area A7, or in a destination area to which the instruments and the surgical instrument sets are sent from the repair area A7.

Examples of Work Information to be Recorded

As has been described above, the work information to be recorded and the items to be recorded vary among the areas A1 to A7. The memory storage device 140 of the system 10 may include, for example, tables (information storage tables) each in a predetermined format for storing the items of work information obtained at each of the areas A1 to A7. The items of the work information obtained at the areas A1 to A7 may be stored in the fields of the tables prepared respectively for the areas A1 to A7.

FIG. 4 is a view illustrating a table 420 that records work information for the collection area A2. FIG. 5 is a view illustrating a table 440 that records work information for the sterilization area A5. FIG. 6 is a view illustrating a table 460 that records work information for the repair area A7. These tables show examples of work information recorded at the respective areas.

In the collection area A2, the instruments of surgical instrument sets are collected from the surgical operation area A1 individually, for example. In the collection area A2, each of the instruments may be collected while the location of collection and the worker are identified and the item-identifying information symbol attached to the instrument is read with the reader 11b. Thus, as illustrated by the table 420 shown in FIG. 4, information is input into columns 421 to 426, which store set ID, instrument ID, parts ID, collection location, worker, and work date and time, respectively. Note that the records of the work information to be recorded at the collection area A2 are not limited to the example shown in FIG. 4. The records of the work information to be recorded at the collection area A2 may include further detailed information.

In the sterilization area A5, the item-identifying information assigned to a bag or a container is read by the reader 11e, for example, to identify the instrument ID of the instrument or the set ID of the surgical instrument set that is enclosed in the bag or the container. Then, in the sterilization area A5, the sterilization method and the sterilization conditions required for the surgical instrument set or the instrument identified by the set ID or the instrument ID are set for the sterilizer. Then, the surgical instrument set or the instrument should be placed into the sterilizer while causing the reader 11e to read the item-identifying information assigned to the bag or the container. For example, in the sterilization treatment, it is often the case that an indicator showing whether appropriate sterilization was performed may be fitted onto the packaging material that encloses the instrument or the surgical instrument set. In that case, the indicator may change its color, for example, under a predetermined condition. In the sterilization area A5, the indicator may be fitted onto the instrument or the surgical instrument set. The fitting of the indicator may also be carried out in the assembling area A4. The item-identifying information assigned to the bag or the container may be read by the reader 11e also when the bag or the container is removed from the sterilizer, and the end time of the sterilization treatment should be recorded.

Thus, as illustrated by the table 440 shown in FIG. 5, information is input to columns 441 to 449, which store set ID, instrument ID, parts ID, packaging material, sterilization method, sterilization condition, effective period, worker, and work date and time, respectively. The records of the work information to be recorded in the sterilization area A5 are not limited to the example of FIG. 5. The record of the work information to be recorded in the sterilization area A5 may include further detailed information. For example, the records of the work information obtained at the sterilization area A5 may include image data of the indicator after the sterilization treatment.

Here, a period of time for which the sterilization treatment remains effective is input into the column 447 that stores effective period.

The effective period of sterilization treatment may be determined from the sterilization method and the sterilization conditions. In this case, the relationship between sterilization method, sterilization conditions, and effective period may be recorded in advance in the master data of the system 10. It is also possible that the effective period of sterilization treatment may be determined from the sterilization method and the sterilization conditions. In that case, the relationship between packaging method, sterilization method, sterilization conditions, and effective period may be prerecorded in the master data of the system 10. For example, when the packaging method, the sterilization method, and the sterilization conditions are input at the sterilization area A5, the effective period may be accordingly input based on the master data.

The column 449 for work date and time may record, for example, the time at which the item-identifying information assigned to the bag or the container has been read by the reader 11e when the sterilization treatment was completed and the bag or the container was taken out of the sterilizer.

As illustrated in FIG. 6, for example, at the repair area A7, items of information are input into columns 461 to 469, which respectively record the following items of information about the instruments and the surgical instrument sets that have been brought into the repair area A7: the instrument IDs and the set IDs of the instruments and the surgical instrument sets, dates and times indicating when they have been brought into the repair area A7, dates and times indicating when they have been brought out from the repair area A7, repair factors that are the factors that have necessitated the repair work, and costs required for the repair work. It is also possible that any appropriate information other than the above-listed items of information may be input. In this preferred embodiment, the information on the workers (user IDs) and the dates and times of the work performed in the repair area A7 are input. However, these items of information may not be necessary. When there are a plurality of items of work information for each of the instruments or the surgical instrument sets, such items may be input for each of the work processes performed.

Thus, in the system 10, the work histories of the instruments, including work information about repair work, are stored in association with the instrument IDs. Also, the work histories of the surgical instrument sets, including work information about repair work, are stored in association with the set IDs. This allows the system 10 to be used to extract the instrument IDs and the set IDs of the instruments and the surgical instrument sets that are under repair, and to provide the user with the information about the status of the instruments and the surgical instrument sets, including the status of repair, for example.

The processor 100 of the system 10 may be configured or programmed to collect the item-identifying information read by the readers 11a to 11g of the respective areas A1 to A7 and the work information stored associated with the item-identifying information. This enables the system 10 to collect the information of the instruments and the surgical instrument sets to be managed by the system 10 at the areas A1 to A6 and to collectively manage the information. In addition, it is possible to extract, for example, the work information indicating when, in which area, and what kind of, work was performed for a certain instrument, in chronological order. For example, when inputting an instrument ID or a set ID into the table 420, the table 440, it is possible to input an instrument ID or a set ID that is obtained by looking up the master data of the instrument IDs and the set IDs based on the item-identifying information read by one of the readers 11a to 11g in the repair area A7 shown in FIGS. 4 to 6.

The processor 100 of the system 10 may collect, for example, the work information recorded at the areas A1 to A7 from the control terminals 13a to 13g arranged respectively in the areas A1 to A7. This allows the processor 100 to store the work histories of the instruments identified by the instrument IDs so that the work histories are associated with the instrument IDs. This also allows the processor 100 to store the work histories of the surgical instrument sets identified by the set IDs so that the work histories are associated with the set IDs.

Thus, the third memory 103 and the fourth memory 104 may be configured or programmed to collect the work information recorded at the areas A1 to A7 from the respective control terminals 13a to 13g. As a result, the information containing the work history of each of the instruments identified by the instrument IDs may be stored in association with the instrument IDs. Likewise, the information containing the work history of each of the surgical instrument sets identified by the set IDs may be stored in association with the set IDs. The work history of each of the instruments and the surgical instrument sets may include work information about repair work.

It should be noted that the work histories of the instruments that are to be stored in association with the instrument IDs need not be stored in a single database for each of the instrument IDs. Also, the work histories of the surgical instrument sets that are to be stored in association the set IDs need not be stored for in a single database each of the set IDs.

For example, the system 10 extracts items of work information from the work information stored in the processor 100 based on an instrument ID, and arranges the extracted items of the work information in chronological order based on the work time, so that the system 10 can obtain the work history of the instrument identified by the instrument ID appropriately. The system 10 also extracts items of work information from the work information stored in the processor 100 based on a set ID, and arranges the extracted items of the work information in chronological order based on the work time, so that the system 10 can obtain the work history of the surgical instrument set identified by the set ID appropriately.

FIG. 7 illustrates an example of a table including data obtained by extracting the work history of a certain instrument. The table 480 shown in FIG. 7 contains items 481 to 489, which respectively indicate instrument ID, area (area ID), worker (user ID), delivery date and time, work date and time, sent-out date and time, packaging method, sterilization method, and effective period, which are extracted consecutively to form a list.

For example, according to the table 480 shown in FIG. 7, an instrument identified by the instrument ID "BM1" is collected in the collection area A2 and thereafter cleaned in the cleaning area A3 at timing k1. Thereafter, the instrument is brought into the repair area A7, in which a predetermined repair work is carried out. Thereafter, the instrument is taken out from the repair area A7 to the assembling area A4, in which assembling work is carried out at timing k3. For a surgical instrument set as well, the work history can be extracted in a similar manner to that shown in FIG. 7. Thus, the work history including the repair work can be obtained for each of the surgical instrument sets.

As already discussed previously, the repair work is outsourced, so it is out of the normal use cycle, surgical operation→collection (sorting)→cleaning→assembling (sealing)→sterilization→storage. However, the system 10 enables the user to easily obtain, for example, information as to whether or not an instrument or a surgical instrument set is sent out for repair.

Thus, the system 10 is able to be configured or programmed to obtain the work histories including the repair work of the instruments and the surgical instrument sets.

Processing in System 10

The system 10 may include, for example, processors as described below.

The first processor 201 is configured or programmed to extract instrument IDs of the instruments under repair based on the work histories of the instruments. For example, when a shortage of instruments used for a surgical operation occurs, the user is able to know whether the cause of the shortage is that the actual number of the instruments in stock is insufficient or that the instruments have been sent out for repair work. The user of the system 10 can easily judge whether to purchase or rent an instrument based on the information obtained from the system 10.

The second processor 202 is configured or programmed to extract set IDs of the surgical instrument sets that are under repair, based on the work histories of the surgical instrument sets. Such a second processor 202 enables the user of the system 10 to, for example, recognize the cause of a shortage of surgical instrument sets based on the information obtained from the system 10, so that the user can easily judge whether to purchase or rent an instrument. It is also possible that the system 10 may set a desired time and the first processor 201 may be configured or programmed to extract instrument IDs of the instruments that are under repair at the set time. It is also possible that the system 10 may set a desired time and the second processor 202 may be configured or programmed to extract set IDs of the surgical instrument sets that are under repair at the set time.

Thus, with the first processor 201 and the second processor 202, the user of the system 10 is able to recognize the instruments and the surgical instrument sets that are under repair at a desired time. For example, when instruments or surgical instrument sets have been rented at a certain time due to a shortage of instruments or surgical instrument sets, for example, the user of the system 10 is able to analyze the cause of shortage of instruments and surgical instrument sets at the time after the event. The user is also able to recognize the numbers and the proportions of the instruments and the surgical instrument sets that are under repair, or the transition of the numbers and the proportions of the instruments and the surgical instrument sets that are under repair. For example, the numbers and the proportions of the instruments and the surgical instrument sets that are under repair may be represented by a pie chart or a bar graph. The transition of the numbers and the proportions of the instruments and the surgical instrument sets that are under repair may be represented by a line chart.

The third processor 203 may be configured or programmed to obtain repair rates of the instruments and the surgical instrument sets. Herein, the repair rate refers to a proportion of a period in which an instrument or a surgical instrument set is under repair work within a predetermined period. For example, the repair rate may be calculated by the equation: Repair rate=Period in which the instrument or the surgical instrument set is under repair/Predetermined period. Accordingly, it is expected that when the repair rate is higher, the proportion of the period in which the instrument or the surgical instrument set is under repair work is correspondingly higher and the utilization rate of the instrument or the surgical instrument set is accordingly lower.

The third processor 203 is configured or programmed enables the system 10 to provide the repair rates of the instruments and the surgical instrument sets to the user. The user is able to recognize, for example, ones of the instruments and the surgical instrument sets that have a higher repair rate. The instruments and the surgical instrument sets that have a higher repair rate result in higher maintenance costs. If that is the case, the user can consider replacement of such instruments and surgical instrument sets with new ones. It is possible to replace the instruments and the surgical instrument sets that have a higher repair rate may be replaced with ones that have a lower repair rate. The system 10 can provide the basis for such judgement to the user.

The third processor 203 may further be configured or programmed to extract an instrument ID indicative of an instrument or a set ID indicative of a surgical instrument set based on the repair rates. For example, the third processor 203 may be configured or programmed to extract instrument IDs of the instruments, or set IDs of the surgical instrument sets, that have a repair rate higher than a predetermined rate. On the contrary, the third processor 203 may be configured or programmed to extract instrument IDs of the instruments, or set IDs of the surgical instrument sets, that have a repair rate lower than a predetermined rate.

Such a third processor 203 enables the user of the system to easily recognize the surgical instrument sets and the surgical instruments that have higher repair rates or lower repair rates.

The third processor 203 may further be configured or programmed to compare the repair rates of the instruments and the surgical instrument sets. This enables the system 10 to provide the user with information that compares the repair rates on an instrument by instrument basis or on a surgical instrument set by set basis, for example, information indicating that the repair rates are different between instruments of the same type or between surgical instrument sets of the same type.

For example, as illustrated in FIG. 3, the first memory 101 may store attribute information in association with the instrument IDs. The second memory 102 may store attribute information in association with the set IDs. In this case, the system 10 may further include a fourth processor 204 configured or programmed to extract instrument IDs of instruments or set IDs of surgical instrument sets, for each type of instrument, for each type of surgical instrument set, or for each attribute.

Herein, the attribute information may be information indicative of a hospital or a medical department that owns the instruments or the surgical instrument sets. In this case, the system 10 is able to inform the user that the repair rate of the instrument or the surgical instrument set is different depending on the hospital or the medical department, even between the instruments of the same type or between the surgical instrument sets of the same type. The attribute information is not limited to hospital or medical department, and may be, for example, information related to the manufacturer and the model of the instrument or the surgical instrument set. In this case, the system 10 is able to inform the user that the repair rate of the instrument or the surgical instrument set is different between the instruments of the same type or between the surgical instrument sets of the same type, depending on the manufacturer or the model. The attribute information is not limited to hospital or medical department, and may be, for example, information related to the manufacturer and the model of the instrument or the surgical instrument set.

The fourth processor 204 may be configured or programmed to obtain repair rates of the instruments and the surgical instrument set for each of the attributes. In this case, the system 10 is able to provide the user with the information about different repair rates between the instruments of the same type or between the surgical instrument sets of the same type, depending on the hospital, the medical department, the manufacturer, or the model. For example, when the repair rate is higher depending on the hospital or the medical department, the user of the system 10 is able to check if the hospital or the medical department has a problem in the manner of use of the instruments or the surgical instrument sets, or to suggest reviewing the manner of use in order to improve the repair rate. Also, when the repair rate is higher depending on the manufacturer or the model, the system 10 may be used to select the manufacturer or the model of the instrument or the surgical instrument set that is to be purchased. [015U] The fourth processor 204 may further be configured or programmed to extract attributes of the instruments and the surgical instrument sets based on the repair rates. In this case, the user of the system 10 is provided with the information related to the attributes of the instruments and the surgical instrument sets that have higher repair rates, such as the hospitals, the medical departments, the manufacturers, and the models that lead to higher repair rates. The user of the system 10 can easily identify the information related to the attributes of the instruments and the surgical instrument sets that have higher repair rates.

In this case, the fourth processor 204 may further be configured or programmed to compare the attributes based on the repair rates. This enables the system 10 to provide information in which the repair rates of the instruments and the surgical instrument sets are compared between different attributes. This enables the user of the system 10 to easily recognize the attributes of the instruments and the surgical instrument sets that lead to higher repair rates, i.e., the hospitals, the medical departments, the manufacturers, and the models that lead to higher repair rates. In this case, the system 10 may be configured or programmed to provide data in which the repair rates are compared between different attributes by, for example, showing the repair rate of each of the attributes by a bar graph. In addition, the system 10 may be configured so that not only the repair rates but also the numbers and the proportions of the instruments under repair and the surgical instrument sets under repair can be compared between different attributes. In this case, it is possible that the numbers and the proportions of the instruments and the surgical instrument sets that are under repair may be represented by a bar graph or a pie chart for different attributes. It is also possible that the transition of the numbers and the proportions of the instruments and the surgical instrument sets that are under repair may be represented by line charts for different attributes.

The fifth processor 205 sets a period Z1 for which the repair rates are to be obtained. In this case, each of the repair rates is obtained as the proportion of a period required for repair of one of the instruments or the surgical instrument sets within the period Z1. The fifth processor 205 allows the user of the system 10 to set the period Z1 for which the repair rates are to be obtained to any desired period. Thus, the system 10 is able to obtain repair rates for a desired period and provide the obtained repair rates to the user. In this case, the user can easily recognize the instruments and the surgical instrument sets that have lower utilization rates due to prolonged repair periods.

In this preferred embodiment, the work information about repair work includes the information about the factor that has necessitated the repair work, as illustrated in FIG. 6. The sixth processor 206 may be configured or programmed to extract at least one of the instrument IDs or at least one of the set IDs, for each of the factors that has necessitated the repair work.

Such a sixth processor 206 extracts instrument IDs of the instruments, or the set IDs of the surgical instrument sets, for different factors that have necessitated the repair work. This enables the user of the system 10 to analyze the instruments and the surgical instrument sets for different factors that have necessitated the repair work.

Further, the seventh processor 207 is configured or programmed to sort periods required by ones of the instruments or ones of the surgical instrument sets for repair by each of the factors that has necessitated the repair work. Such a seventh processor 207 enables the user of the system 10 to analyze the time period required for the repair for each of the factors that necessitates the repair work.

Thus, the system 10 is able to provide the user with various types of information that are usable for the analysis of the repair factors and the improvement of the work.

In this preferred embodiment, the work information about repair work includes information about the cost required for the repair work, as illustrated in FIG. 6. The eighth processor 208 is configured or programmed to obtain a cost required for repair of an instrument or a surgical instrument set based on the work information about the repair work.

In this case, the eighth processor 208 may be configured or programmed to obtain a cost required for the repair work within a predetermined period Z2, for example. In this case, when the period Z2 is set to, for example, the part one year period, the costs required for the repair work of the instruments and the surgical instrument sets are totaled over the past one year period, to obtain the costs required for the repair work of the instruments and the surgical instrument sets in the past one year period. The period Z2 is not limited to the past one year, but may be set to any desired period.

The eighth processor 208 may also be configured or programmed to compare the instruments and the surgical instrument sets based on the obtained cost. That is, the eighth processor 208 may be configured or programmed to calculate and compare the costs required for the repairs of some of the instruments or the surgical instrument sets.

The process of the comparing may be performed so that, for example, the instruments and the surgical instrument sets to be compared, and the costs required for the repair work are arranged in a table format, and the table is displayed on the display 12. In addition, the system 10 may be configured or programmed to change the order of display so that the instruments and the surgical instrument sets are arranged in order of the cost required for the repair work. In addition, the system 10 may be configured or programmed to change the colors of the columns that display the instruments and the surgical instrument sets according to the cost required for the repair work. Also, the instruments and the surgical instrument sets may be displayed in different colors so that the instruments or the surgical instrument sets with higher costs are indicated by darker colors.

Thus, the costs required for repair work are calculated for respective instruments and surgical instrument sets, and the calculated costs are compared. As a result, items of the information about the instruments and the surgical instrument sets that require higher costs are extracted and provided to the user of the system 10. This allows the user of the system 10 to easily recognize which of the instruments and the surgical instrument sets require higher cost for repair.

The system 10 may be configured or programmed to extract a contractor that is able to carry out the repair at the lowest cost, based on the costs required for the repair work of each of the instruments by different contractors. The system 10 may also be configured or programmed to create and display a list table that shows workers of the repair work performed for the instruments and costs required for the repair work. Also, the system 10 may be configured or programmed to total the repair cost and the purchase cost of each of the instruments as the maintenance cost, or to divide the maintenance cost by the number of times of use to calculate and display the cost per one time of use for each of the instruments.

This serves to provide the source of judgement as to whether an instrument should be purchased or rented.

The system 10 may be configured or programmed to be able to summarize the repair costs for different workers and different outside contractors based on the user IDs, and to compare the repair costs and the repair periods required for the same instrument between outside contractors.

This may serve to easily select the most suitable contractor.

Thus, the system 10 includes the third memory 103 to store work histories of the instruments each identified by a respective one of the instrument IDs, each of the work histories stored in association with the respective one of the instrument IDs and including work information about repair work, and the fourth memory 104 to store work histories of the surgical instrument sets each identified by a respective one of the set IDs, each of the work histories stored in association with the respective one of the set IDs and including work information about repair work.

Such a system 10 is able to obtain the work histories of the instruments and the surgical instrument sets, including the work information about the repair work performed on the instruments and the surgical instrument sets. Furthermore, the system 10 may be configured or programmed to obtain the numbers, the proportions, and the repair rates of the instrument and the surgical instrument sets that are under repair, based on the work histories of the instruments and the surgical instrument sets. This serves to provide the numbers, the proportions, and the repair rates of the instruments and the surgical instrument sets that are under repair to the user of the system 10.

The system 10 herein causes the processor 100 to aggregate information to perform a predetermined process. Each of the control terminals 13*a* to 13*g* may be configured or programmed to acquire information from the processor 100 as well, so as to perform a similar process to the process performed by the processor 100. In other words, each of the control terminals 13*a* to 13*g* may be configured or programmed to function as the system 10 on its own. The control terminals 13*a* to 13*g* may also be configured or programmed to bidirectionally communicate with the processor 100 to cooperate with the processor 100, and to display required information with the control terminals 13*a* to 13*g*, upon receiving the result computed by the processor 100. Each of the control terminals 13*a* to 13*g*, defining and functioning as a client terminal, may be configured or programmed to be a tablet terminal equipped with a camera. In this case, the camera fitted in the tablet terminal may be configured or programmed to function as a reading unit of each of the readers 11*a* to 11*g*. It is also possible that the screen of the tablet terminal may be configured or programmed to function as one of the displays 12*a* to 12*h*.

In addition, the system 10 is able to collectively manage the information about the surgical instrument sets and the instruments that are used in a plurality of hospitals by, for example, gathering the information into the processor 100. In this case, the surgical operation area A1, the collection area A2, and the like are provided in each of the hospitals. In the system 10, the control terminals 13*a* to 13*g* in the respective areas A1 to A7 and the processor 100 may be connected to each other so as to allow bidirectional communication with each other. It is also possible that, by cloud computing technology, the work histories of the instruments and the surgical instrument sets as well as the utilization rates of the instruments and the surgical instrument sets, for example, may be made available to an external terminal 21 connected to the system 10.

For example, as illustrated in FIGS. 1 and 2, the external terminal 21 may be connected to the system 10 through the communication network 14. The work histories of the instruments and the surgical instrument sets, the utilization rates of the instruments and the surgical instrument sets, and the like may be distributed from the system 10 to a predetermined terminal through the communication network 14 at predetermined timing. In addition, data such as the numbers of instruments and surgical instrument sets under repair and the repair rates may be displayed on the external terminal 21 in a predetermined form (also referred to as a dashboard).

The external terminal 21 may be a terminal that is not installed in the areas A1 to A7. For example, the system 10 may be accessed from a terminal installed in, for example, a department of a hospital that takes charge of administrative work, accounting, inventory control, procurement of instruments and surgical instrument sets, and the like, which does not carry out such work as surgical operation and collection, to acquire the information of the instruments and the surgical instrument sets managed by the system 10. In addition, the external terminal 21 may be a portable terminal that is connectable with the communication network 14, such as a smartphone, a tablet computer, or a laptop computer. In this case, the system 10 can be accessed from any desired location to acquire the information of the instruments and the surgical instrument sets managed by the system 10.

The system 10 may incorporate a required authentication process and a required function restriction process to the external terminal 21 as needed. In that case, the system 10 may be configured or programmed to prepare a website that is browsable by a web browser installed in the external terminal 21. The system 10 may be configured or programmed to perform, through the prepared website, an authentication process for the external terminal 21 and provide a predetermined service in response to a request from the external terminal 21, for example.

As described thus far, the system 10 may be configured or programmed to cause the external terminal 21 to display various types of data that can be provided by the system 10 in response to a request from the external terminal 21 connected via the communication network 14. Various types of data that can be provided by the system 10 are not limited to the examples described herein. Examples of the data that can be provided by the system 10 may include information stored in storage devices in the system 10, information computed or extracted through various kinds of processes performed by the system 10, and the graphs and lists created by the system 10.

Hereinabove, various preferred embodiments of the surgical instrument set and instrument management systems proposed in this disclosure have been described, but it should be understood that the surgical instrument set and instrument management systems proposed in this disclosure is not limited to the preferred embodiments described hereinabove. Various modifications and alterations of the surgical instrument set and instrument management systems may be possible. In addition, the features, structures, or steps described herein may be omitted where appropriate, or may be combined in any suitable combinations, unless specifically stated otherwise.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A surgical instrument set and instrument management system comprising:
    a first memory to store instrument IDs associated in a one-to-one correspondence with instruments;
    a second memory to store set IDs associated in a one-to-one correspondence with surgical instrument sets, each of the surgical instrument sets including a plurality of instruments;
    a third memory to store work histories of the instruments each identified by a respective one of the instrument IDs, each of the work histories stored in association with the respective one of the instrument IDs and including work information about repair work; and
    a fourth memory to store work histories of the surgical instrument sets each identified by a respective one of the set IDs, each of the work histories stored in association with the respective one of the set IDs and including work information about repair work.

2. The surgical instrument set and instrument management system according to claim 1, further comprising a first processor configured or programmed to extract at least one of the instrument IDs that indicates one of the instruments that is under repair, based on the work histories of the instruments.

3. The surgical instrument set and instrument management system according to claim 1, further comprising a second processor configured or programmed to extract at least one of the set IDs that indicates one of the surgical instrument sets that is under repair, based on the work histories of the surgical instrument sets.

4. The surgical instrument set and instrument management system according to claim 1, further comprising a fourth processing section configured or programmed to obtain repair rates of the instruments and the surgical instrument sets.

5. The surgical instrument set and instrument management system according to claim 4, wherein the third processor is further configured or programmed to extract at least one of the instrument IDs or at least one of the set IDs, based on the repair rates.

6. The surgical instrument set and instrument management system according to claim 4, wherein the third processor is configured or programmed to compare the repair rates of the instruments and the surgical instrument sets.

7. The surgical instrument set and instrument management system according to claim 4, further comprising:
    a fifth processor configured or programmed to set a period (Z1) for which the repair rates are to be obtained; wherein
    each of the repair rates is obtained as the proportion of a period required for repair of one of the instruments or the surgical instrument sets within the period (Z1).

8. The surgical instrument set and instrument management system according to claim 1, wherein
    the first memory is provided to store information related to attributes in association with the instrument IDs; and
    the second memory is provided to store information related to attributes in association with the set IDs; and
    the system further comprising a fourth processor configured or programmed to extract one of the instrument IDs or the set IDs for each type of the instruments, each type of the surgical instrument sets, or each of the attributes.

9. The surgical instrument set and instrument management system according to claim 8, wherein the fourth processor is configured or programmed to obtain repair rates of the instruments or the surgical instrument sets for each of the attributes.

10. The surgical instrument set and instrument management system according to claim 9, wherein the fourth processor is further configured or programmed to extract attributes of the instruments and the surgical instrument sets based on the repair rates.

11. The surgical instrument set and instrument management system according to claim 9, wherein the fourth processor is further configured or programmed to compare the attributes based on the repair rates.

12. The surgical instrument set and instrument management system according to claim 1, wherein the work information about the repair work includes information related to a factor that has necessitated the repair work.

13. The surgical instrument set and instrument management system according to claim 12, further comprising a sixth processor configured or programmed to extract at least one of the instrument IDs or at least one of the set IDs, for each of the factors that has necessitated the repair work.

14. The surgical instrument set and instrument management system according to claim 12, further comprising a seventh processor configured or programmed to sort periods required by ones of the instruments or ones of the surgical instrument sets for repair by each of the factors that has necessitated the repair work.

15. The surgical instrument set and instrument management system according to claim 1, wherein
    the work information about the repair work includes information about a cost required for the repair work; and
    the system further comprising an eighth processor configured or programmed to obtain a cost that has been required for the repair work of the instruments and the surgical instrument sets based on the work information about the repair work.

16. The surgical instrument set and instrument management system according to claim 15, wherein the eighth processor is configured or programmed to obtain a cost that has been required for the repair work within a predetermined period (Z2).

17. The surgical instrument set and instrument management system according to claim 15, wherein the eighth processor is configured or programmed to compare the instruments and the surgical instrument sets with each other based on the obtained costs.

18. The surgical instrument set and instrument management system according to claim 1, further comprising:
- a plurality of readers disposed respectively in predetermined work spaces; wherein
- each of the instruments includes item-identifying information;
- the first memory is provided to store the item-identifying information of each of the instruments in association with the instrument IDs; and
- the second memory is provided store the item-identifying information of each of the instruments in association with the instrument IDs and the set IDs; and the system further comprising:
- a tenth processor configured or programmed to, if one of the instrument IDs is identified when the item-identifying information is identified by one of the readers, add information about work performed for one of the instruments identified by the one of the instrument IDs to the work history of the one of the instruments in association with the identified one of the instrument IDs, and also configured or programmed to, if one of the set IDs is identified when the item-identifying information is identified by one of the readers, add information about work performed for one of the surgical instrument sets identified by the one of the set IDs to the work history of the one of the surgical instrument sets in association with the identified one of the set IDs.

* * * * *